US012778780B2

(12) United States Patent
Decker

(10) Patent No.: US 12,778,780 B2
(45) Date of Patent: Nov. 3, 2026

(54) SYSTEMS AND METHODS FOR DUAL MOTION STENT DEPLOYMENT

(71) Applicant: KONINKLIJKE PHILIPS N.V., Eindhoven (NL)

(72) Inventor: Cedar Decker, Albertville, MN (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 647 days.

(21) Appl. No.: 18/026,928

(22) PCT Filed: Sep. 14, 2021

(86) PCT No.: PCT/EP2021/075169

§ 371 (c)(1),
(2) Date: Mar. 17, 2023

(87) PCT Pub. No.: WO2022/069210

PCT Pub. Date: Apr. 7, 2022

(65) Prior Publication Data

US 2024/0009013 A1 Jan. 11, 2024

Related U.S. Application Data

(60) Provisional application No. 63/085,177, filed on Sep. 30, 2020.

(51) Int. Cl.
*A61F 2/966* (2013.01)

(52) U.S. Cl.
CPC .................................... *A61F 2/966* (2013.01)

(58) Field of Classification Search
CPC ........ A61F 2/2436; A61F 2/95; A61F 2/9517; A61F 2/966; A61F 2/9661; A61F 2/9662; A61F 2002/9665

(Continued)

(56) References Cited

U.S. PATENT DOCUMENTS 5,707,376 A * 1/1998 Kavteladze ............... A61F 2/90 623/1.11
9,724,223 B2 8/2017 Dooley
(Continued)

FOREIGN PATENT DOCUMENTS

CN 108245291 A 7/2018
EP 2651345 B1 5/2018

OTHER PUBLICATIONS

International Search Report and Written Opinion Dated Jan. 5, 2022 For International Application No. PCT/EP2021/075169 Filed Sep. 14, 2021.

*Primary Examiner* — Kankindi Rwego

(57) ABSTRACT

Systems and methods for deployment of a compressed expandable structure in a vessel lumen by inserting a catheter configured at a proximal end with dual shuttles; rotating a main drive shaft coupled via a set of drive gears to a set of catheter gears, enabling by rotation of the main drive shaft translated movement back and forth of the set of catheter gears wherein the set of catheter gears includes a pair of catheter gears each threaded in opposite directions for bidirectional movement to advance the inner lumen shuttle and the outer sheath shuttle in opposite directions; and deploying, by the bidirectional movement of the catheter gears, by the simultaneous withdrawal and insertion of the shuttle's outer sheath and inner lumen, the compressed expandable structure at a deployment location nearer to the catheter's distal end for more accurate placement to the treatment area's location.

4 Claims, 6 Drawing Sheets

(58) Field of Classification Search
USPC .......................................... 606/108; 623/1.11
See application file for complete search history.

(56) References Cited

U.S. PATENT DOCUMENTS

| | | | | |
|---|---|---|---|---|
| 10,433,994 | B2 | 10/2019 | Green | |
| 10,583,021 | B2 | 3/2020 | Daly | |
| 2003/0191516 | A1* | 10/2003 | Weldon | A61F 2/95 623/1.12 |
| 2012/0172963 | A1 | 7/2012 | Ryan | |
| 2014/0135909 | A1* | 5/2014 | Carr | A61F 2/2436 623/2.11 |
| 2014/0180381 | A1 | 6/2014 | Kelly | |
| 2016/0074191 | A1 | 3/2016 | Cummins | |
| 2016/0120677 | A1 | 5/2016 | Heanue | |
| 2018/0221182 | A1 | 8/2018 | Shumer | |
| 2019/0321075 | A1 | 10/2019 | Painchaud | |

* cited by examiner

SYSTEMS AND METHODS FOR DUAL MOTION STENT DEPLOYMENT

CROSS REFERENCE TO RELATED APPLICATIONS

This application is the U.S. National Phase application under 35 U.S.C. § 371 of International Application No. PCT/EP2021/075169 filed Sep. 14, 2021, which claims the benefit of U.S. Provisional Patent Application No. 63/085,177 filed Sep. 30, 2020. These applications are hereby incorporated by reference herein.

TECHNICAL FIELD

The technical field generally relates to endovascular procedures and more particularly relates to systems and methods for stent deployment in a vessel lumen.

BACKGROUND

Endovascular procedures can entail the use and delivery of an expandable metal tubular support structures (e.g., stents) via intravascular devices in the treatment of intravascular disease, arterial and venous, as well as for the treatment of larger anatomical regions such as the esophagus. The accurate permanent or temporal placement of the expandable metal tubular support structures is critical in achieving the desired outcomes for the diseased regions of a vessel as well as avoiding damage to the healthy regions of the vessel.

The design of these intravascular devices routinely may include the following three elements: An expandable structure (such as a stent or filter) that can be compressed down sufficiently to fit inside a catheter suitable for intravascular use; An inner shaft or lumen, down to which the expandable structure is compressed; and An outer sheath to cover and maintain the compressed structure until it has been tracked to the desired treatment position and the expandable structure is released.

A technical problem that is presented is the control and proper placement of the expandable structure. Expandable structures inherently struggle with placement accuracy due to the change in length caused by the expanding diameter, as the structure is released from its compressed state. As the structure expands during deployment, the length shortens, making the positioning of the ends difficult. The present disclosure describes deployment mechanisms that could be incorporated into a catheter-based delivery system to counteract the geometric changes in an expandable structure to achieve more accurate placement.

Accordingly, technologically improved systems and methods for placement of expandable structures in the treatment in a vessel lumen are desirable. The following disclosure provides these technological enhancements, in addition to addressing related issues.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

In one exemplary embodiment, a method for deployment of a compressed expandable structure in a vessel lumen is provided. The method includes inserting a catheter configured at a proximal end with dual shuttles for deploying a stent at a distal end of the catheter within the vessel lumen at a location of a treatment area; configuring dual shuttles at the catheter's proximal end with an inner lumen shuttle attached to the compressed expandable structure and an outer sheath shuttle covering the compressed expandable structure; rotating a main drive shaft coupled via a set of drive gears to a set of catheter gears, enabling by rotation of the main drive shaft translated movement back and forth of the set of catheter gears wherein the set of catheter gears includes a pair of catheter gears each threaded in opposite directions for bidirectional movement to advance the inner lumen shuttle and the outer sheath shuttle in opposite directions; in response to the rotation of the main drive shaft, simultaneously withdrawing, by the pair of catheter gears, an outer sheath by the outer sheath shuttle that covers the compressed expandable structure at the catheter's distal end while inserting by the inner lumen shuttle the compressed expandable structure at the catheter's distal end; and deploying, by the bidirectional movement of the catheter gears, by the simultaneous withdrawal and insertion of the shuttle's outer sheath and inner lumen, the compressed expandable structure at a deployment location nearer to the catheter's distal end for more accurate placement to the treatment area's location.

In various exemplary embodiments, the method further includes in response to the simultaneous withdrawal and insertion of the shuttle's outer sheath and inner lumen at the deployment, configuring a difference in a rate of motion of withdrawal of the shuttle's outer sheath to the insertion of the shuttle's inner lumen that corresponds to an expansion of the compressed expandable structure. The method further includes configuring the difference in the rate of motion to account for a change in length that results from an expansion of the compressed expandable structure. The method further includes configuring the rate of motion based on a pitch of a pair of oppositely threaded drive gear sets, which can account for the change in length that results from an expansion in the compressed expandable structure. The method further includes increasing the difference in pitch of the pair of oppositely threaded gear sets to account for an increased length that results from the expansion of the compressed expandable structure. The method further includes decreasing the difference in pitch of the pair of oppositely threaded drive gear sets to account for a decreased length that results from the expansion in of the compressed expandable structure. The method further includes configuring the pair of the drive gear sets in a first part at a proximal location of the shaft and a second part at a distal location of the shaft. The method further includes configuring the pair of catheter gear sets into a first part and a second part for pulling the stent back into the outer sheath or pushing the stent forward out of the outer sheath.

The method further includes configuring the first and second parts of catheter gears to correspond to the first and second parts of the drive gears of drive shaft gears wherein rotation of either set of drive shaft gears translates into a forwarding or backward movement of the inner lumen shuttle and the outer sheath shuttle wherein the amount of forwarding movement or backward movement is determined by the first part and the second drive gear pitch. The compressed expandable structure includes one or more of a set, including a stent, a filter, and tubular support placed in a vessel lumen or body cavity. The deployment of the compressed expandable structure further includes inserting the catheter to the location of the treatment area based on a marker longitudinally located at the distal end of the catheter that enables positioning of the catheter at a deployment point prior to the location of the treatment area. The method includes upon deployment at the point prior to the location of the treatment area, exposing the compressed expandable structure by withdrawing the outer sheath thereby allowing expansion of the compressed expandable structure to reach a wall of the vessel lumen; and in response to the deployment of an entire compressed expandable structure, retracting the catheter via an open diameter of a no longer compressed expandable structure.

In another exemplary embodiment, a system for deployment of a compressed expandable structure in a vessel lumen is provided. The system includes a catheter deployment device that includes a catheter coupled with dual shuttles at a proximal end to enable the deployment of a stent at the distal end of the catheter which is inserted within a vessel lumen at a location of a treatment area; a first cable connected to an inner lumen shuttle coupled to an inner lumen that the compressed expandable structure is affixed and a second cable connected to an outer sheath shuttle coupled to an outer sheath that covers the compressed expandable structure wherein the shuttle's inner lumen and the outer sheath is positioned on the distal end of the catheter; a thumbwheel coupled to the catheter that when actuated, draws each cable in the opposite direction to cause the shuttle's inner lumen to advance in an opposite direction to the shuttle's outer sheath; in response to the rotation of the thumbwheel, the shuttle's outer sheath covering the compressed expandable structure at the catheter's distal end is withdrawn while simultaneously the shuttle's inner lumen attached to the compressed expandable structure at the catheter's distal end is inserted; and in the deployment by the simultaneous withdrawal and insertion of the shuttle's outer sheath and inner lumen, the compressed expandable structure is placed at a deployment location nearer to the catheter's distal end for more accurate positioning to the treatment area's location.

The system further includes in response to the simultaneous withdrawal and insertion of the shuttle's outer sheath and inner lumen at the deployment, the catheter deployment device is configured with a difference in a rate of motion of withdrawal of the shuttle's outer sheath shuttle to the insertion of the shuttle's inner lumen that corresponds to an expansion of the compressed expandable structure. The system further includes the catheter deployment device is configured for a difference in the rate of motion to account for a change in length that results from an expansion in the compressed expandable structure. The system further includes the catheter deployment device that is configured with the rate of motion based on the diameter of the thumbwheel and the diameter of each pulley to account for the change in length that results from an expansion in the compressed expandable structure.

In yet another exemplary embodiment, a method for deployment of a compressed expandable structure in a vessel lumen is provided. The method includes inserting a catheter coupled with dual shuttles at a proximal end of the catheter for stent deployment with the vessel lumen at a location of a treatment area; configuring the shuttle by coupling a first part of a ratchet to an inner lumen shuttle connected to an inner lumen to hold the compressed expandable structure and by coupling a second part of the ratchet to an outer sheath shuttle coupled to an outer sheath that covers the compressed expandable structure wherein the shuttle's inner lumen and outer sheath are attached to the distal end of the catheter; actuating the rachet to cause the rachet's first part to advance the shuttle's inner lumen in an opposite direction to the shuttle's outer sheath shuttle upon deployment; in response to the actuation of the rachet, simultaneously causing the catheter to withdraw the shuttle's outer sheath covering the compressed expandable structure at the catheter's distal end while inserting the shuttle's inner lumen attached to the compressed expandable structure at the catheter's distal end; and deploying, by the catheter, by the simultaneous withdrawal and insertion of the shuttle's outer sheath and inner lumen, the compressed expandable structure at a deployment location nearer to the catheter's distal end for more accurate placement to the treatment area's location.

In various exemplary embodiments, the method includes deploying both the shuttle's outer sheath and inner lumen by a single operation of a rachet arm of the ratchet for positioning of the compressed expandable structure at the deployment location nearer to the catheter's distal end.

The compressed expandable structure includes one or more of a set, including a stent, a filter, and tubular support placed in a vessel lumen or body cavity. The method further includes inserting the catheter at the location of the treatment area based on a marker longitudinally located at the distal end of the catheter that enables positioning of the catheter at a deployment point prior to the location of the treatment area.

Furthermore, other desirable features and characteristics of the system and method will become apparent from the subsequent detailed description and the appended claims, taken in conjunction with the accompanying drawings and the preceding background.

BRIEF DESCRIPTION OF THE DRAWINGS

The present application will hereinafter be described in conjunction with the following drawing FIGURES, wherein like numerals denote like elements, and.

DETAILED DESCRIPTION

Figure 1:
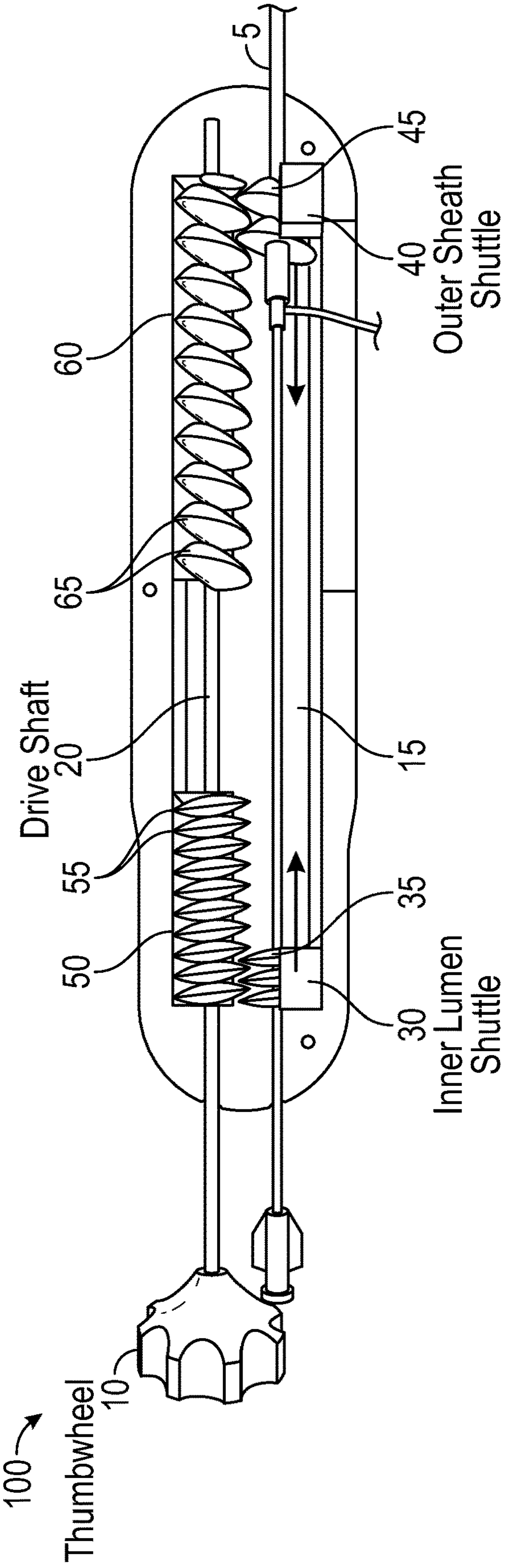
FIG. 1 is a block diagram of a system for stent deployment system in a vessel lumen, in accordance with an exemplary embodiment.

The following detailed description is merely illustrative in nature and is not intended to limit the embodiments of the subject matter or the application and uses of such embodiments. As used herein, the word "exemplary" means "serving as an example, instance, or illustration." Thus, any embodiment described herein as "exemplary" is not necessarily to be construed as preferred or advantageous over other embodiments. The embodiments described herein are exemplary embodiments provided to enable persons skilled in the art to make or use the invention and not to limit the scope of the invention that is defined by the claims. Furthermore, there is no intention to be bound by any expressed or implied theory presented in the preceding technical field, background, summary, or the following detailed description.

As mentioned, a technical problem is presented in controlling the placement of stents using a catheter. The features described in the present disclosure are directed to the use of simultaneous, opposing motion to counteract the geometric changes in the expanding structure. The opposing motions may be equal in speed and/or magnitude, or they may be differentiated based on unique factors in the design of the expandable structure or delivery system. Additionally, the opposing motion may be independently activated to achieve precise positioning of both the leading and trailing ends of the expandable structure. This configuration is achieved additionally by the positioning of markers on a delivery system (i.e., the catheter shaft) to indicate a location to the user prior to deployment of the stent. The marker of the catheter dictates to the user when the opposing motions will be active, either independently or in tandem, to ensure that the expanding structure is accurately placed in the region of the vessel indicated by the markers on the catheter shaft, prior to the deployment. The embodiments with the diagrams in the following section demonstrate potential mechanisms for achieving simultaneous and opposing motion in a catheter-based stent deployment system.

The term "catheter" as used herein generally refers to a tube that can be inserted into a body cavity, duct, lumen, or vessel, such as the vasculature system. In most uses, a catheter is a relatively thin, flexible tube ("soft" catheter), though, in some uses, it may be a larger, solid-less flexible—but possibly still flexible—catheter ("hard" catheter). In some uses, a catheter may contain a lumen along part or all of its length to allow the introduction of other catheters or guidewires. An example of a catheter is a sheath.

Currently, the vast majority of intravascular procedures are performed under X-ray guidance. Unfortunately, an x-ray provides very limited information for the deployment of an expandable stent in the vessel anatomy. This lack of information results in a number of challenges for clinicians in the placement of the stent after deployment.

Exemplary embodiments provide a technical solution to this problem in the form of a stent deployment system (FIG. 1) embodying novel rules, vascular anatomy design factors, and recommended treatment protocols for deploying a compressed tubular structure in a vessel lumen, as follows.

The disclosed stent deployment system 100 forms the described stent deployment features by the use of simultaneous and opposing motion to counteract the geometric changes in the expanding structure. The opposing motions may be equal in speed and/or magnitude, or can be differentiated based on unique factors in the design of the expandable structure or delivery system. Additionally, the opposing motions may be independently activated to achieve precise positioning of both the distal and proximal ends of the expandable stent structure.

Provided embodiments include an improved stent deployment procedure in which the physician gains access to the desired artery/vein, and inserts the catheter, and tracks it to the position the physician would like to place a stent at a marker band at the end of the catheter. The marker band is used to position the catheter-based deployment system at the desired landing position of the stent. The outer sheath is pulled back, exposing the stent and allowing it to expand until it reaches the vessel wall. Once the entire stent is deployed, the catheter is drawn back through the open diameter of the stent and removed Provided embodiments enable by pushing the stent forward as it is being deployed, the change in length is compensated by the stent deployment structure or configuration, and this configuration results in an accurately placed stent without requiring active intervention from the physician.

The FIGURES and descriptions below provide more detail.

Turning now to FIG. 1, in an embodiment, the system for a stent deployment by a catheter in a vessel lumen 100 (also referred to herein as "system" 100) is depicted as associated with a vessel lumen (not shown). In various embodiments, the vessel lumen is a blood vessel in a patient. As mentioned, system 100 embodies bidirectional motion to deploy a compressed tubular structure in a vessel lumen. Catheter 5 may be manually operated by a user; manual input can include a direction and a placement operation.

The direction is generally, from the perspective of the distal tip of the catheter 5, forward and aft, longitudinally, within a vessel lumen. The stent deployment system 100 includes a thumbwheel 10, an inner lumen shuttle 30, and an outer sheath shuttle 40. A set of gears (50,60) is attached to a main drive shaft 20. The gear set is composed of a set of gears 50 on the proximal end of the main drive shaft 20 and another set of gears 60 on the distal end of the main drive shaft 20. Each of the set of drive shaft gears 50, 60 is threaded with an adjacent set of catheter gears 35, 45 of another shaft 15 that by rotation enables translates to an inner lumen shuttle 30 attached on the proximal end moving in either direction. The inner lumen shuttle 30 is configured with a set of catheter gears 35. The set of drive shaft gears 50 of the main drive shaft 20 is interleaved with the set of catheter gears 35 of the inner lumen shuttle 30. Likewise, the set of drive shaft gears 60 of the main drive shaft 20 is interleaved with the set of catheter gears 45 of the outer sheath shuttle 40. Upon manual actuation of the thumbwheel 10, the main drive shaft 20 rotation, will result in translation of motion longitudinally back and forth of the corresponding set of catheter gears (35,45) that coupled together on the secondary shaft 15 and the motion (i.e. movement on the shaft 15) is determined by the pitch of the drive shaft gears (50,60). The catheter gears 35, 45 will not actually rotate with the main drive shaft 20 but will move back and forth (screw-like manner) in a longitudinal direction based on which way the main drive shaft 20 is rotated. The inner lumen and outer sheath shuttles can move in either direction based on the direction of rotation of the main drive shaft 20 which means that the stent can be either pulled back into the outer sheath or pushed forward out of the outer sheath if the user desires. Further, either of the catheter (or shuttle) gears 35, 45 can be disengaged and reengaged with the main drive shaft 20 set of gears (50 or 60) to stop and start the motion of either the inner lumen 30 or outer sheath 45, as the user desires. This allows further customization as to the manner and location for the stent to be deployed. Both of these functions (re-sheath and stop/start) can also be configured and enabled to apply to the pulley embodiments described in FIGS. 2A, 2B, and the ratchet embodiment in FIG. 4 described later in the disclosure.

The thumbwheel 10 can rotate in a clockwise (or a counterclockwise) direction depending on the initial default pitch configuration and interleaving of both sets of gears. In the case of a clockwise rotation of the thumbwheel 10, the inner lumen shuttle 30 via rotational torque exerted by the set of gears 50 connected to the drive shaft 20 would drive (or translate) in the inner lumen part of the catheter longitudinally moved forward which would result in pushing the inner shuttle of the catheter 5 forward to place the compressed stent at a location for treatment in the vessel lumen. At the same time (i.e., simultaneously), the clockwise rotation of the thumbwheel 10 would cause or translate in the outer sheath shuttle 40 to be driven in the opposite direction to the inner lumen shuttle 30 on the adjacent shaft that would result in the outer sheath shuttle 40 uncovering and releasing the compressed stent (i.e. unsheathe process). Hence, as the thumbwheel 10 is turned, the oppositely threaded gears 50, 60 on the drive shaft 20 rotate, pulling the inner shuttle 30 and the outer shuttle 40 in opposite directions. The difference in the rate of motion between the two shuttles enables an accurate accounting or compensation for changes in the length of the deployed stent (i.e., change in length due to expansion of the compressed stent). The rate of motion is determined by the pitch of the threaded components. For example, the set of threaded gears 50 has a pitch 55, and the opposite gear set 60 has a pitch 65.

Figure 2:
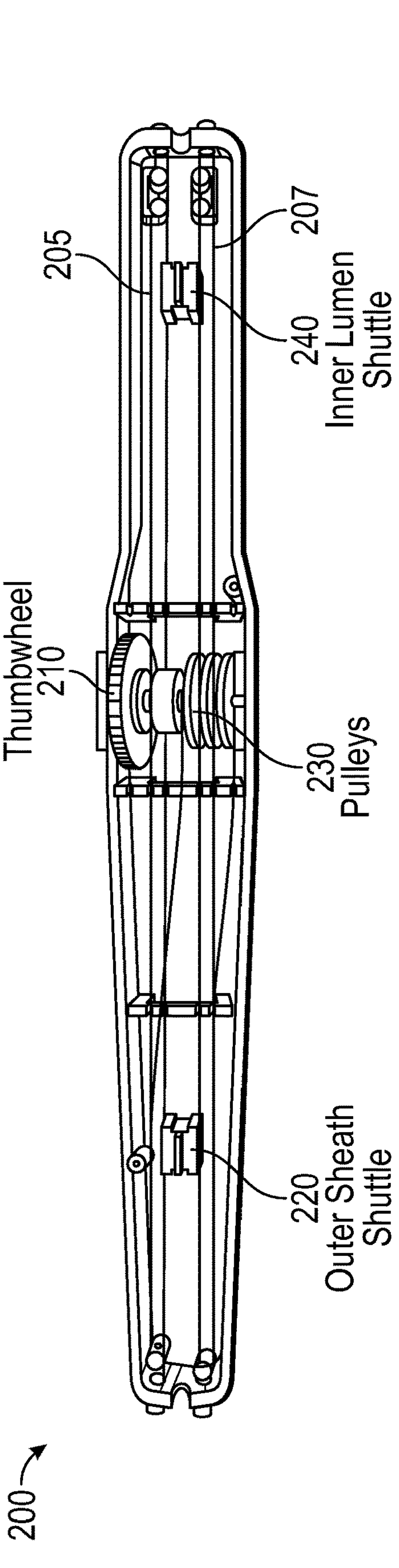
FIG. 2 illustrates an exemplary diagram of an embodiment of the stent deployment system with pulleys in accordance with an embodiment.

Turning to FIG. 2, an exemplary diagram of another embodiment of the stent deployment system is illustrated in accordance with an embodiment. In FIG. 2, there is shown a pulley and cable stent deployment system 200, which includes a thumbwheel 210, an outer sheath shuttle 220, pulleys 230, and an inner lumen shuttle 240. Similar to FIG. 1, as the thumbwheel 210 is turned or rotated in either a clockwise or counterclockwise direction, outer lumen shuttle 220 is pulled in the opposite direction to the inner lumen shuttle 240 during the deployment at the end of the catheter (not shown). The difference in the rate of motion between the two shuttles again accounts for the change in length of the deployed stent. Turning the thumbwheel 210 draws the sets of connecting cables (205, 207) through the pulleys 230, causing the shuttles to move in opposite directions. The rate of motion of each of the shuttles (220, 240) is determined by the diameter of the thumbwheel 210 and the pulleys 230. Hence, the greater the diameter of the thumbwheel 210 or the pulleys 230, the more the cables can be drawn by incremental rotations of each component (i.e., the thumbwheel 210 and the pulley 230).

Figure 3:
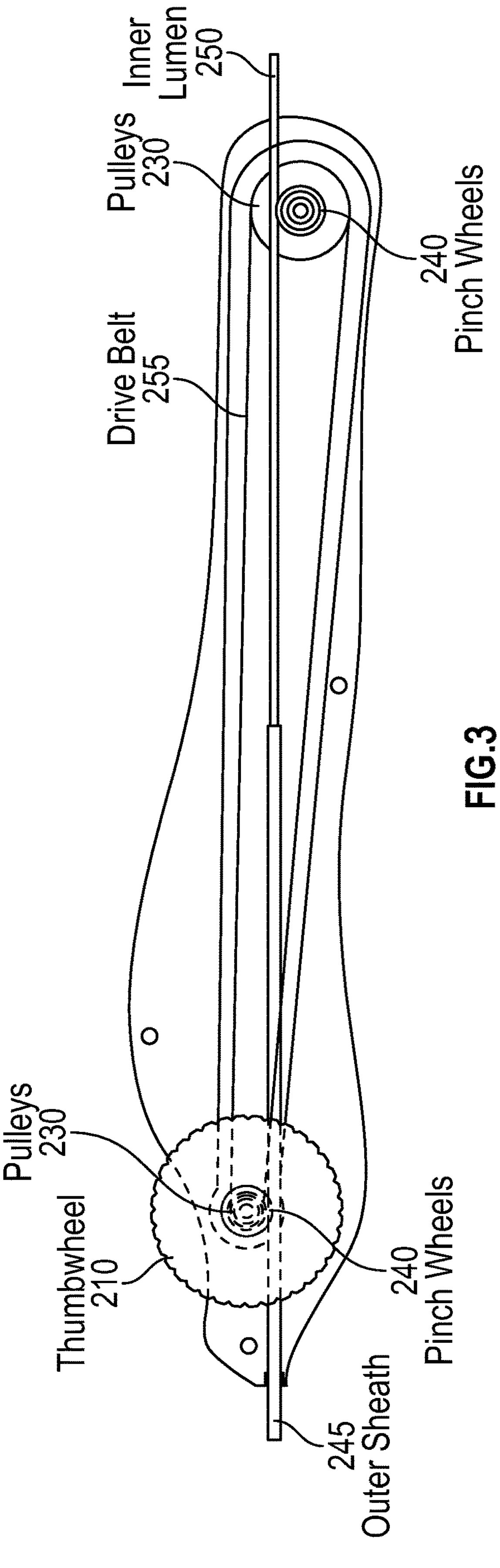
FIG. 3 illustrates an exemplary diagram of an embodiment of the stent deployment system with pulleys in accordance with an embodiment.

Turning to FIG. 3, in another exemplary embodiment using pulley, the stent deployment system of FIG. 3 incorporates two pulleys 230 connected by a drive belt 255 or cable. Each pulley 230 is driven by the thumbwheel 210 and can rotate in opposite directions. Each pulley 230 is also coupled to pinch wheels 240 that contact the outer sheath 245 and inner lumen 250 independently. The rotation of the thumbwheel 210, pulleys 230, and pinch wheels 240 configurations result in the outer sheath 245 and inner lumen 250 moving in opposite directions. The relative rates of motion of the inner lumen 250 and outer sheath 245 are determined by the ratio of their respective pulley 230 diameters. The motion of the inner lumen 250 and outer sheath 245 can be reversed by rotating the thumbwheel 210 in an opposite direction, thus the stent can be re-sheathed if desired. It is also possible to activate the motion of the inner lumen 250 and outer sheath 245 separately in an exemplary embodiment, so the breadth of functionalities (i.e. all the applicable functionalities) that are enabled, applicable and described with respect to the exemplary embodiments illustrated in FIG. 1 and FIG. 5, can also be enabled, configured, and implemented in a manner that applies to the pulley based stent deployment system of the exemplary embodiments described and illustrated in FIGS. 2 and 3.

Figure 4:
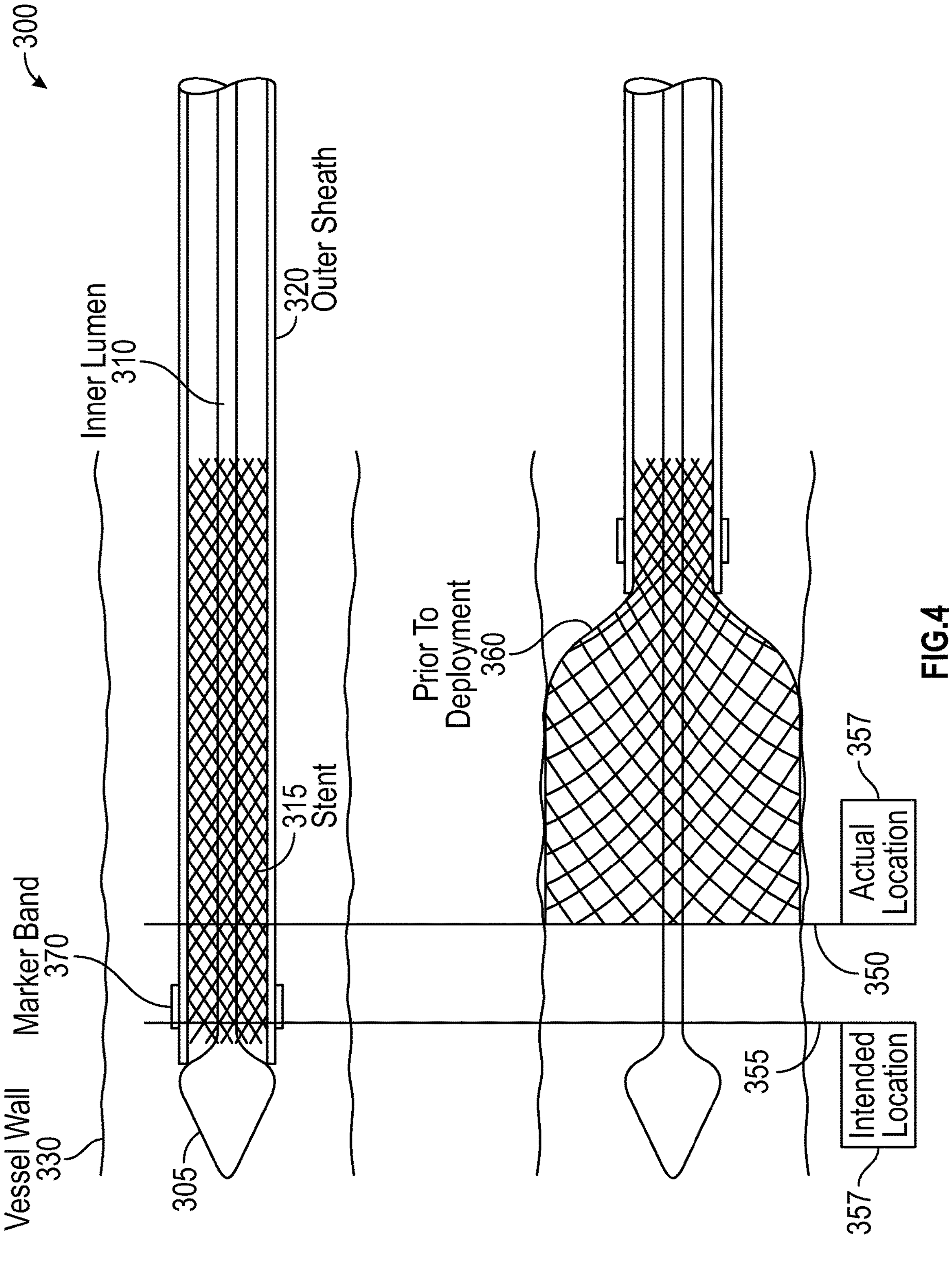
FIG. 4 illustrates an exemplary diagram of compressed stent placement and an expansion of the compressed stent at deployment that can cause the stent location to recede from the desired location without compensation for the length reduction in accordance with an embodiment.

FIG. 4 is an exemplary diagram of compressed stent placement and an expansion of the compressed stent at deployment that can cause the stent location to recede from the desired location without compensation for the length reduction in accordance with an embodiment. FIG. 4 in the exemplary diagram depicts the intended location 355 and illustrates the actual location 350 that results from the stent length shortening as it expands. In other words, if this change 357, that results in length due to the stent expansion is not accounted for, as shown in FIG. 4, during the stent deployment procedure, the resultant stent placement will not occur at the intended location 355 but be placed at the actual location 357. In FIG. 4, the user (i.e., a physician or other medical personnel) may follow an exemplary stent deployment procedure. For example, the user may gain access to the desired artery/vein. The user may insert the catheter 305 and track the catheter 305 visually using a display device (not shown) until the distal end of the catheter 305 is near or at a proximal location to the desired position would like to place the stent (the intended location 355).

A marker band 370 at the end of the catheter 305 is used to position the catheter 305 based on the desired landing position 355 of the stent 315. The outer sheath 320 is pulled back, exposing the stent 315 and allowing the stent 315 to expand 360 until it reaches vessel wall 330. Once the entire stent 315 is deployed, the catheter 305 is drawn back through the open diameter of the stent 315 and removed. By pushing the stent 315 forward as it is being deployed, the change in length 357 can be accounted for, resulting in an accurately placed stent 315 without requiring further active intervention from the user. The action of pushing the stent forward by the rotation of the shaft and simultaneously withdrawing, by the catheter, the outer sheath shuttle that covers the compressed expandable structure at the catheter's distal end while inserting the inner lumen shuttle attached to the compressed expandable structure at the catheter's distal end enables a better positioning of the stent deployment. This results in deploying, by the catheter, by the simultaneous withdrawal and insertion of the shuttle's outer sheath and inner lumen, the compressed expandable structure at a deployment location nearer to the catheter's distal end for more accurate placement to the treatment area's location.

Figure 5:
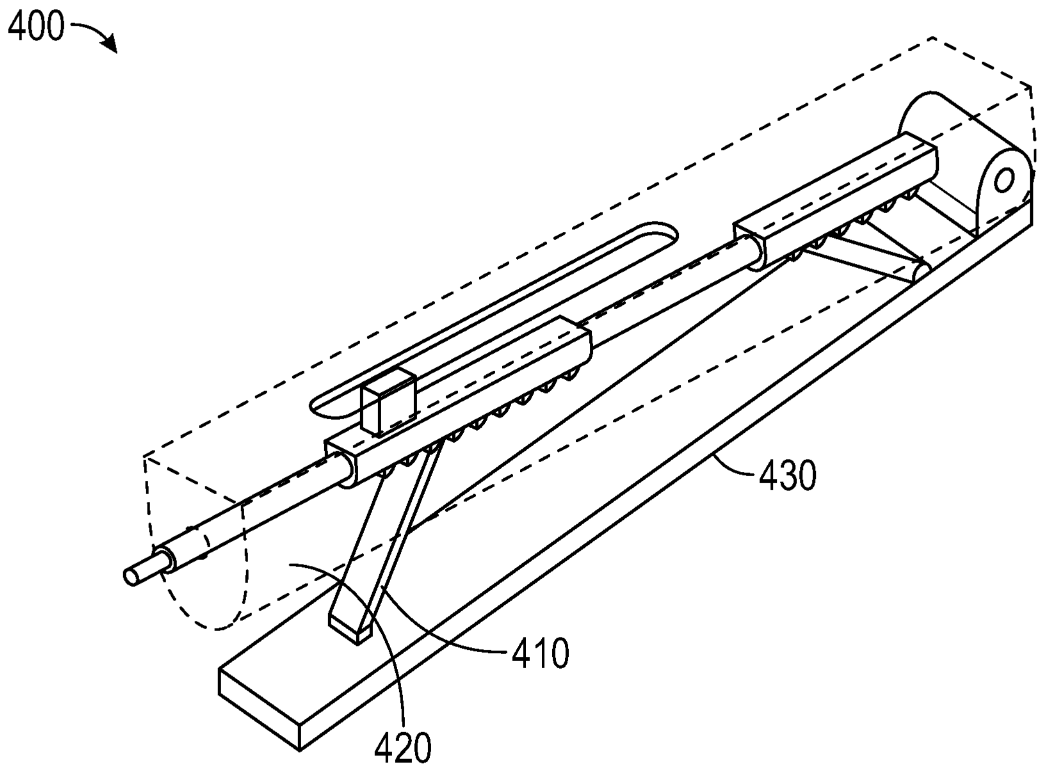
FIG. 5 illustrates another exemplary diagram of another embodiment of the stent deployment system in accordance with an embodiment.

Turning to FIG. 5, an exemplary diagram of another embodiment of the stent deployment system using a ratchet deployment system is illustrated in accordance with an embodiment. FIG. 5 illustrates a ratchet deployment system 400 rather than a thumbwheel or pulley stent deployment system of FIGS. 1-3. In FIG. 5, the ratchet stent deployment system 400 includes a single ratchet arm 430 coupled to a first part 410 and to a second part 420 that pull the outer sheath shuttle (not shown) and the inner lumen shuttle in opposite directions. The length and angle of each part can determine the difference in the rate of motion between the two shuttles. The ratchet arm 430 enables a user in one step actuation to deploy the compressed stent at the desired location by closing the ratchet arm 430. Hence, a convenient one-step stent deployment system using the ratchet arm 430 is described.

Figure 6:
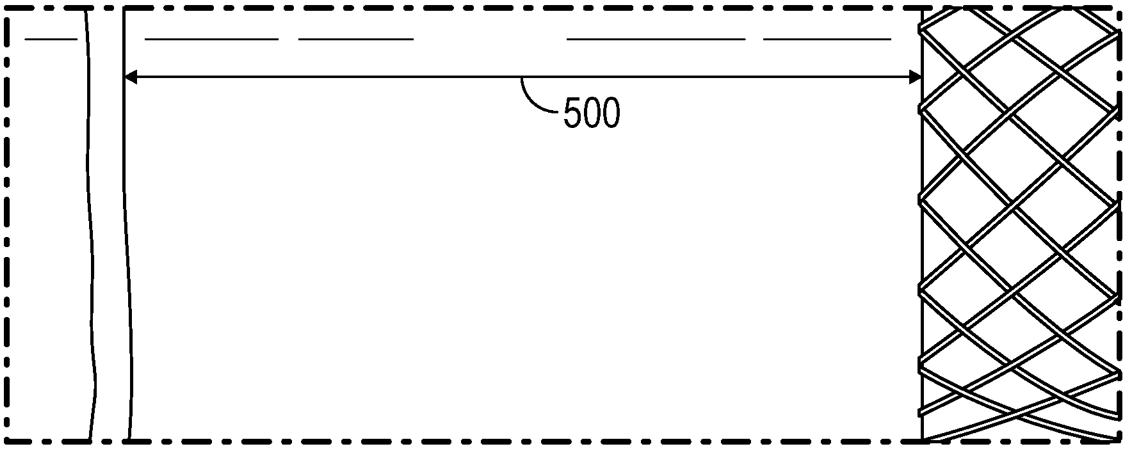
FIG. 6 illustrates an exemplary diagram of a comparison of a reduction in distance of the compressed stent placement in accordance with an embodiment.
Figure 7:
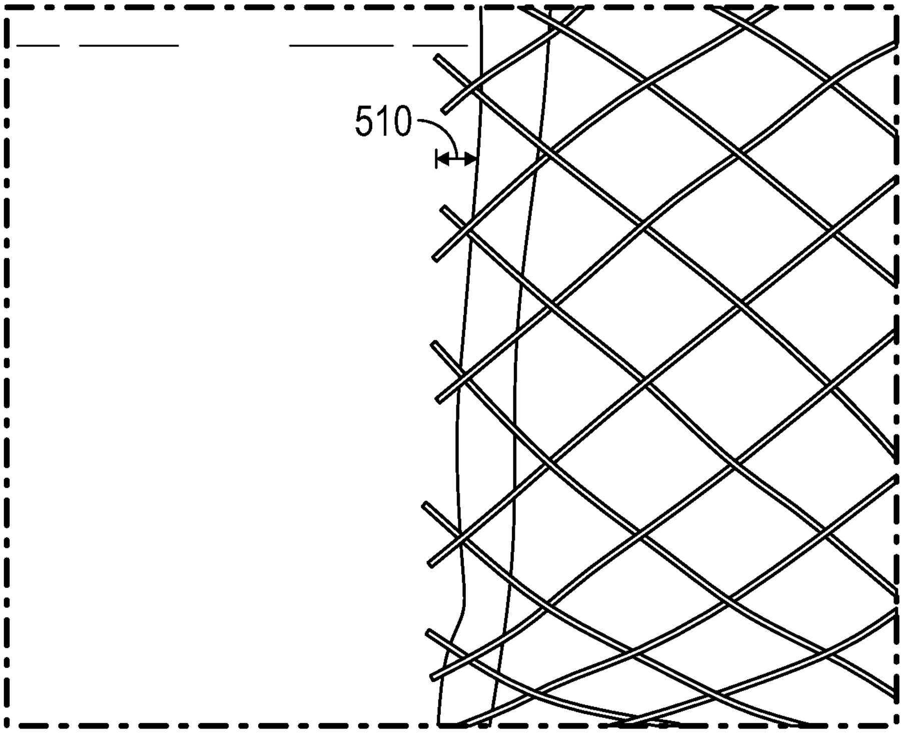
FIG. 7 illustrates an exemplary diagram of a comparison of a reduction in distance of the compressed stent placement in accordance with an embodiment.

FIGS. 6 and 7 are exemplary diagrams of a comparison of a reduction in distance of the compressed stent placement in accordance with an embodiment. In FIG. 6, there is illustrated a distance 500 of approximately 23.4 mm that results when the stent is deployed without the dual motion at the deployment location. In FIG. 7, there is illustrated a reduced distance 510 of 0.49 mm that results when the stent is deployed with the dual motion resulting in a better result and closer to the desired deployment location.

Figure 8:
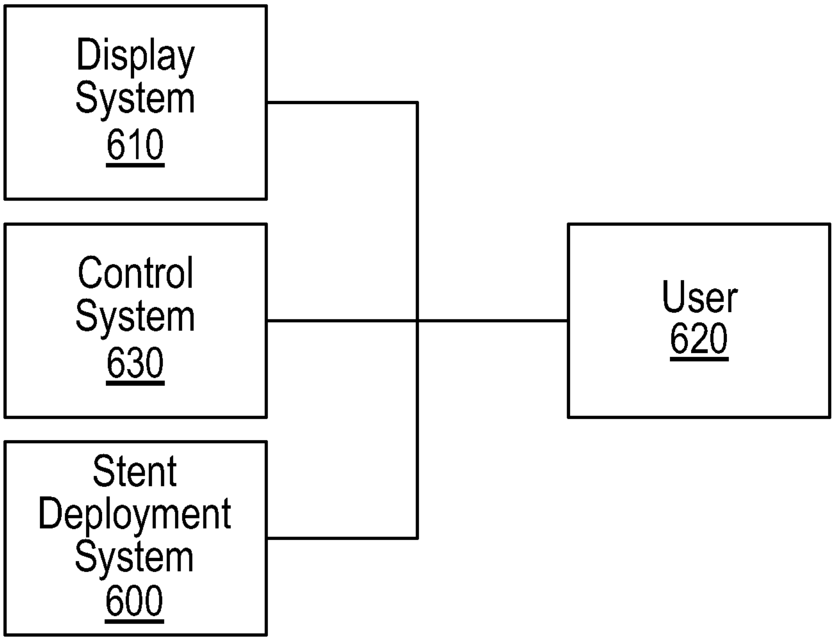
FIG. 8 illustrates an exemplary block of an exemplary display system that implemented with the stent deployment system in accordance with an embodiment.

FIG. 8 is a block diagram showing an exemplary display system that is implemented with the stent deployment system in accordance with an embodiment. In FIG. 8, the user 620 via the display system 610 can view the marker band at the end of the catheter to position the catheter based on the desired landing position of the stent. Once at the desired location, user 620 can actuate the stent deployment system 600 using the exemplary configurations shown in FIGS. 1-3 and 5 to enable the outer sheath to be pulled back, exposing the stent and allowing the stent to expand until it reaches the vessel wall. The process can be visually monitored by user 620 on the display system 610 until the entire stent is deployed, and then user 620 would extract the catheter through the open diameter of the stent and until it is completely removed. In various embodiments described herein, the display system 610 may present two- or three-dimensional images and may be realized on one or more electronic display devices cooperatively configured. Renderings on the display system 610 may be processed by a graphics system, components of which may be integrated into the display system 610 and/or be integrated within another control system 630. Display methods also include various formatting techniques for visually distinguishing objects from among other similar objects. For example, the control system 630 can be used in conjunction with the stent deployment system 600 to determine that the catheter is positioned against a vascular blockage such as a piece of plaque. The control system 630 can also determine that the catheter is passing through the healthy vessel to the desired location for deployment.

Figure 9:
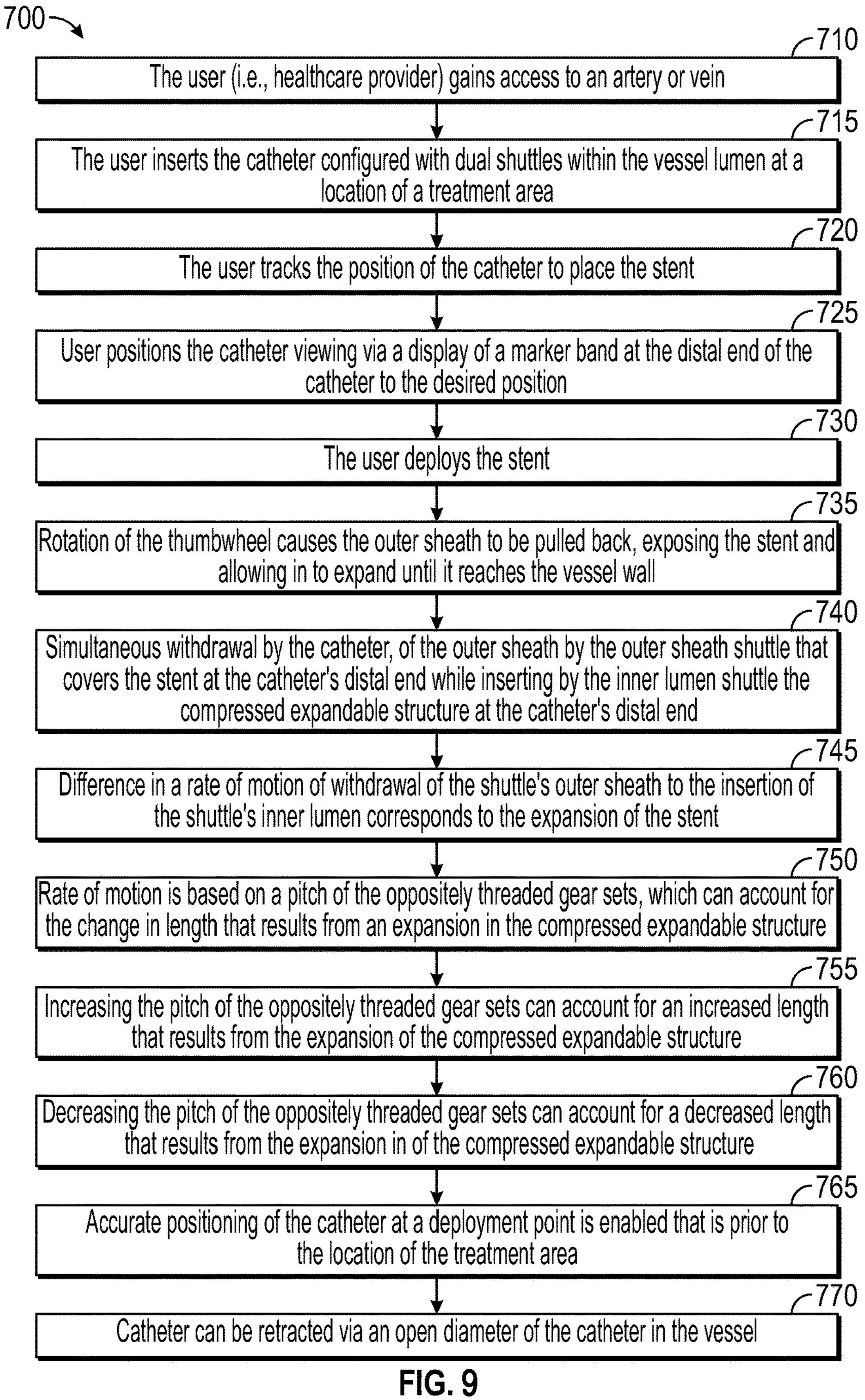
FIG. 9 illustrates an exemplary flow chart for a method system for a stent deployment system in a vessel lumen, in accordance with an exemplary embodiment.

FIG. 9 illustrates an exemplary flowchart of the stent deployment system in accordance with various embodiments. In an exemplary embodiment, FIG. 9 illustrates a method for the deployment of a compressed expandable structure in a vessel lumen. At task 710, the user (i.e., healthcare provider) gains access to an artery or vein. At task 715, the user inserts the catheter that is configured at a proximal end with dual shuttles for deploying a stent at a distal end of the catheter within the vessel lumen at a location of a treatment area. At task 720, the user tracks the position of the catheter to place the stent. The dual shuttles at the catheter's proximal end have an inner lumen shuttle attached to the stent (i.e., the compressed expandable structure) and an outer sheath shuttle covering the stent. At task 725, the user positions the catheter viewing via a display of a marker band at the distal end of the catheter to the desired position. At task 730, the user deploys the stent. For example, the user can, in an exemplary deployment system, rotate a thumbwheel of a drive shaft, which results in translation of motion to a corresponding set of catheter gears that are coupled and whose motion is determined by the pitch of the drive shaft gears coupled to the drive shaft. The catheter gears will not actually rotate with the main drive shaft but will move back and forth based on which way the main drive shaft is rotated. The shuttles can move in either direction based on the direction of rotation of the main drive shaft, which means that the stent can be either pulled back into the outer sheath or pushed forward out of the outer sheath if the user desires. At task 735, the rotation of the thumbwheel causes the outer sheath to be pulled back, exposing the stent and allowing it to expand until it reaches the vessel wall. That is, at task 735, rotating the thumbwheel will cause the stent to advance by the translated motion to the inner lumen shuttle and the outer sheath shuttle in opposite directions. Further, either of the catheter (or shuttle) gears 35, 45 can be disengaged and reengaged with the main drive shaft set of gears to stop and start the motion of either the inner lumen or outer sheath, as the user desires. This allows further customization as to the manner and location for the stent to be deployed. Both of these functions (re-sheath and stop/start) can also be configured and enabled to apply to the pulley embodiments described in FIGS. 2, 3, and the ratchet embodiment in FIG. 5. At task 740, the rotation of the shaft results in simultaneous withdrawal by the catheter, of the outer sheath by the outer sheath shuttle that covers the stent at the catheter's distal end while inserting by the inner lumen shuttle the compressed expandable structure at the catheter's distal end. At task 745, at the stent deployment, a difference in the rate of motion of withdrawal of the shuttle's outer sheath to the insertion of the shuttle's inner lumen corresponds to the expansion of the stent. The difference in the rate of motion can account for a change in length that results from an expansion of the compressed expandable structure. At task 750, the rate of motion is based on a pitch of the oppositely threaded gear sets, which can account for the change in length that results from an expansion in the compressed expandable structure. At task 755, increasing the difference in pitch of the oppositely threaded gear sets can account for an increased length that results from the expansion of the compressed expandable structure. At task 760, decreasing the difference in pitch of the oppositely threaded gear sets can account for a decreased length that results from the expansion of the compressed expandable structure. At task 765, by inserting the catheter to the location of the treatment area based on a marker longitudinally located at the distal end of the catheter, more accurate positioning of the catheter at a deployment point is enabled that is prior to the location of the treatment area. At task 770, upon deployment at the point prior to the location of the treatment area, and the exposing of the stent by withdrawing the outer sheath and advancing the inner lumen, this allows the expansion of the stent to reach a wall of the vessel lumen and then the catheter can be retracted via an open diameter of the catheter in the vessel.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate the interchangeability of hardware, various illustrative components, blocks, modules, and steps have been described above generally in terms of their functionality. Whether such functionality is implemented as hardware or software depends upon the application and design constraints imposed on the overall system.

Skilled artisans may implement the described functionality in varying ways for each application, but such implementation decisions should not be interpreted as causing a departure from the scope of the present invention. In addition, those skilled in the art will appreciate that the embodiments described herein are merely exemplary implementations.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. When "or" is used herein, it is the logical or mathematical or, also called the "inclusive or." Accordingly, A or B is true for the three cases: A is true, B is true, and A and B are true. In some cases, the exclusive "or" is constructed with "and;" for example, "one from the set A and B" is true for the two cases: A is true, and B is true.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples and are not intended to limit the scope, applicability, or configuration of the invention in any way. Rather, the foregoing detailed description will provide those skilled in the art with a convenient road map for implementing an exemplary embodiment of the invention. It is understood that various changes may be made in the function and arrangement of elements described in an exemplary embodiment without departing from the scope of the invention as set forth in the appended claims.

What is claimed is:

1. A system for deployment of a compressed expandable structure in a vessel lumen, comprising:

a catheter deployment device comprising:

a catheter coupled with a dual shuttle at a proximal end to enable the deployment of the compressed expandable structure at a distal end of the catheter which is inserted within the vessel lumen at a location of treatment area;

a first cable connected to an inner lumen shuttle of the dual shuttle coupled to an inner lumen to which the compressed expandable structure is affixed and a second cable connected to an outer sheath shuttle of the dual shuttle coupled to an outer sheath that covers the compressed expandable structure wherein the inner lumen and the outer sheath are positioned on the distal end of the catheter;

a thumbwheel coupled to the catheter that when rotated, is configured to draw each cable in an opposite direction to cause the inner lumen to advance in the opposite direction to the outer sheath;

in response to a rotation of the thumbwheel, the outer sheath covering the compressed expandable structure at the catheter's distal end is configured to be withdrawn while simultaneously the inner lumen attached to the compressed expandable structure at the catheter's distal end is configured to be inserted; and in the deployment by simultaneous withdrawal and insertion of the shuttle's outer sheath and inner lumen, the compressed expandable structure is configured to be placed at a deployment location nearer to the catheter's distal end for more accurate positioning to the treatment area's location.

2. The system of claim 1, further comprising, in response to the simultaneous withdrawal and the insertion of the shuttle's outer sheath and inner lumen at the deployment, the catheter deployment device is configured with a difference between a rate of motion of the withdrawal of the outer sheath and a rate of motion of the insertion of the inner lumen that corresponds to an expansion of the compressed expandable structure.

3. The system of claim 2, further comprising:

the catheter deployment device is configured for the difference in the rate of motion to account for a change in length that results from the expansion in the compressed expandable structure.

4. The system of claim 3, further comprising:

the catheter deployment device is configured with the rate of motion based on a diameter of the thumbwheel and a respective diameter of a pully for each cable to account for the change in length that results from the expansion in of the compressed expandable structure.

* * * * *